US006855349B2

(12) United States Patent
Greaves et al.

(10) Patent No.: US 6,855,349 B2
(45) Date of Patent: Feb. 15, 2005

(54) METHOD FOR SIMULTANEOUS EXTRACTION OF ESSENTIAL OILS AND ANTIOXIDANTS FROM *LABIATAE* SPECIES AND THE EXTRACT PRODUCTS THEREOF

(75) Inventors: John A. Greaves, Ankeny, IA (US); Friedhelm Brinkhaus, Urbandale, IA (US); James E. Haworth, Des Moines, IA (US)

(73) Assignee: Kemin Industries, Inc., Des Moines, IA (US)

( * ) Notice: Subject to any disclaimer, the term of this patent is extended or adjusted under 35 U.S.C. 154(b) by 57 days.

(21) Appl. No.: 09/206,458

(22) Filed: Dec. 7, 1998

(65) Prior Publication Data

US 2003/0049332 A1 Mar. 13, 2003

(51) Int. Cl.$^7$ .............................................. A61K 35/78
(52) U.S. Cl. ........................ 424/745; 424/725; 424/747
(58) Field of Search .............................. 424/745, 195.1, 424/725, 747

(56) References Cited

U.S. PATENT DOCUMENTS

| | | | |
|---|---|---|---|
| 3,669,679 | A | 6/1972 | Panzer |
| 3,950,266 | A | 4/1976 | Chang |
| 4,354,035 | A | 10/1982 | Christ |
| 4,358,442 | A | 11/1982 | Wirtz-Peitz |
| 4,380,506 | A | 4/1983 | Kimura |
| 4,450,097 | A | 5/1984 | Nakatani |
| 4,638,095 | A | 1/1987 | Chang |
| 5,176,913 | A | 1/1993 | Honerlagen |
| 5,209,870 | A | 5/1993 | Todd |
| 5,256,700 | A | 10/1993 | Aeschbach |
| 5,433,949 | A | 7/1995 | Kahleyss |
| 5,512,285 | A | 4/1996 | Wilde |
| 5,525,260 | A | 6/1996 | Aeschbach |

FOREIGN PATENT DOCUMENTS

| | | | |
|---|---|---|---|
| EP | 0616821 A1 | | 9/1994 |
| EP | 94301199.9 | | 9/1994 |
| GB | 9622136.1 | | 10/1996 |
| GB | 2308358 | | 6/1997 |
| GB | 2324050 | * | 10/1998 |
| JP | 55018436 A | | 2/1980 |
| JP | 58217584 A | | 12/1983 |
| JP | 60224629 A | | 11/1985 |
| JP | 61024522 A | | 2/1986 |
| JP | 61027910 A | | 2/1986 |
| JP | 02092258 A | | 4/1990 |
| WO | PCT/US94/13253 | | 7/1995 |
| WO | WO 95/18834 | | 7/1995 |
| WO | PCT/GB95/00554 | | 10/1995 |
| WO | WO 95/26794 | | 10/1995 |
| WO | PCT/US96/06250 | | 11/1996 |
| WO | WO 96/34534 | | 11/1996 |

OTHER PUBLICATIONS

Amaro–Luis, J.M., Herrera, R., and Luis, J.G. "Abietane Diterpenoids from *Salvia Chinopeplica*", Phytochemistry, vol. 47, No. 5 pp. 895–897, 1998.

Luis, J.G., Quinones, W., Grillo, T.A., and Kishi, M.P., "Diterpenes from the Aerial Part of *Salvia Columbariae*", Phytochemistry, vol. 35, No. 5, pp. 1373–1374, 1994.

Kuzmenko, A.I., Morozova, R.P., Nikolenko, I.A., Donchenko, G.V., Richheimer, S.L., and Bailey, D.T., "Chemiluminescence determination of the in vivo and in vitro antioxidant activity of RoseOx and carnosic acid", J. Photochem.Photobiol.B: Biol. 48, 63–67, 1999.

Aruoma, O.I., Spencer, P.E., Rossi, R., Aeschbach, R., Khan, A., Mahmood, N., Munoz, A., Murcia, A., Butler, J., and Halliwell, B., "An Evaluation of the Antioxidant and Anti–viral Action of Extracts of Rosemary and Provencal Herbs", Food and Chemical Toxicology 34, pp. 449–456, 1996.

Pedersen, J.A., "Distribution and taxonomic implications of some phenolics in the family Lamiaceae determined by ESR spectroscopy", Biochemical Systematics and Ecology, pp. 229–253. 2000.

Skoula, M., Abbes, J.E., and Johnson, C.B., "Genetic variation of volatiles and rosmarinic acid in populations of *Salvia fruticosa* mill growing in Crete", Biochemical Systematics and Ecology 28, pp. 551–561, 2000.

Aruoma, O.I., Halliwell, B., Aeschbach, R., and Loligers, J., "Antioxidant and pro–oxidant properties of active rosemary constituents: carnosol and carnosic acid", Xenobiotica, vol. 22, No. 2, pp. 257–268, 1992.

Wenkert, E., Fuchs, A., and McChesney, D., "Chemical Artifacts from the Family Labiatae", Indiana University, 1965.

Aruoma, O. I., B. Halliwell, R. Aeschbach, and J. Loligers, "Antioxidant and pro–oxidant properties of active rosemary constituents: carnosol and carnosic acid," Xenobiotica (1992) 22:257–268.

Chang, S. B., B. Ostric–Matijasevic, C–L Huang, and OA–L Hsieh, "Natural antioxdants from rosemary and sage," J. Food Sci. (1977) 42:1102–1106.

Wenkert, E., A. Fuchs, J. D. McChesney, "Chemical artifacts from the family labiate," J. Org. Chem. (1965) 30:2931–2934.

* cited by examiner

Primary Examiner—Christopher R. Tate
(74) Attorney, Agent, or Firm—Kent Herink; Daniel Rosenberg; Davis Law Firm

(57) ABSTRACT

An increase in specific antioxidant activity of extracts from rosemary (*Rosemarinus officinalis*) is obtained by the use of a blend of tetrafluoroethane and acetone in the extraction process. A blend of tetrafluoroethane, acetone and methanol improves total yield. A tetrafluoroethane and acetone blend has higher efficacy but comparatively lower yields. The methods yield a liquid and oily antioxidant extract that is readily mixed with a liquid product such as soybean oil for addition to animal feeds and human food. The methods simultaneously yield pharmaceutical grade essential oils in high yields.

9 Claims, 13 Drawing Sheets

METHOD FOR SIMULTANEOUS EXTRACTION OF ESSENTIAL OILS AND ANTIOXIDANTS FROM *LABIATAE* SPECIES AND THE EXTRACT PRODUCTS THEREOF

BACKGROUND OF THE INVENTION

1. Field of the Invention

The invention relates generally to a method for simultaneous extraction of essential oils and antioxidants from organic material, more particularly organic material from the Lamiaceae (or Labiatae) family, including rosemary (*Rosemarinus officinalis*) and, more specifically, to a method of simultaneous extraction of essential oils and antioxidants from species of the family Labiatae, in particular, rosemary, using solvent blends and which yields a liquid, oily extract containing antioxidants and a liquid extract containing essential oils. The extract containing antioxidants is readily mixed with an edible oil for addition to animal feeds and human food. The essential oils are pharmaceutical grade.

2. Background of the Prior Art

Worldwide demand for natural antioxidants has been rising due to safety concerns about synthetic food and feed additives and the public perception that natural food and feed supplements provide certain health benefits. The most important natural antioxidants being exploited commercially today are tocopherols. Tocopherols have a potent ability to inhibit lipid peroxidation in vivo by trapping peroxy-radicals (Burton, G. W., and K. U. Ingold (1989), in Vitamin E: Biochemistry and Health Implications, edited by A. T. Diplock, L. J. Machlin, L. Packer and W. A. Pryor, The New York Academy of Sciences, New York, pp. 7–22). Various herbal extracts for use as natural antioxidants are being explored. Possibilities include the extraction of rosemary or other botanical sources. Such new antioxidants may play a role in combating carcinogenesis as well as the aging process, and may be applicable in the nutraceutical industry.

Among the various natural extracts available in the market are rosemary extracts, which are reported to be highly effective in retarding lipid oxidation and protecting living cells from the damaging oxidative stress (Chen, Q., H. Shi and C-T Ho (1992), "Effects of rosemary extracts and major constituents on lipid oxidation and soybean lipoxygenase activity", J Am Oil Chem Soc 69: 999–1002; Wong, J. W., K. Hashimoto and T. Shibamoto (1995), "Antioxidant activities of rosemary and sage extracts and vitamin E in a model meat system", J Agric Food Chem 43: 2707–2712). These extracts are described as being superior to vitamin E, a well-known natural antioxidant and food supplement, in many food model systems (Lolinge, J. (1983), Natural antioxidants in Allen, J. C. and R. J. Hamilton eds, Rancidity in Foods, Elsevier Applied Science, London, Chapter 6). However, opposite findings are also documented. Wong et al. (1995) revealed that vitamin E is more effective than rosemary extract in a cooked beef homogenate. Additionally, rosemary extract is shown to be a synergist of vitamin E in stabilizing or retarding oxidation in sardine oil and fish muscle (Fang, X. and S. Wanda (1993), "Enhancing the antioxidant effect of α-tocopherol with rosemary extract in inhibiting catalyzed oxidation caused by $Fe^{2-}$ and hemoprotein", Food Res Int 26: 405–411; Wanda, S. and X. Fang (1992), "The synergistic antioxidant effect of rosemary extract and α-tocopherol in sardine oil model system and frozen-crushed fish meat", J Food Process Preserv 16: 263–274).

As to the extraction of rosemary, many authors report that polar solvents yield extracts with higher antioxidant activities (Chang, S. S., B. Ostric-Matijasevic, C-L Huang and OA-L Hsieh (1977), "Natural antioxidants from rosemary and sage", J Food Sci 42: 1102–1106). Chen et al. (1992) found that hexane extracts of rosemary contained a higher content of carnosic acid and carnosol than methanol extracts do. Carnosic acid and carnosol are the effective antioxidant molecules in rosemary. Carnosic acid and carnosol have been suggested to account for over 90% of the antioxidant activity of rosemary extracts (Aruoma, O. I, B. Halliwell, R. Aeschbach and J. Loligers (1992) "Antioxidant and pro-oxidant properties of active rosemary constituents: carnosol and carnosic acid", Xenobiotica 22: 257–268). Antioxidant molecules in general, and rosemary antioxidants specifically, are by nature labile molecules especially when exposed to heat and/or air. During the harvest, the drying, and the regular solvent extraction of rosemary, some oxidation is likely to occur. Through a process of chemical reactions, carnosic acid, the naturally-occurring antioxidant molecule in rosemary, is believed to be the precursor to carnosol and many other antioxidants found therein (Wenkert, E., A. Fuchs, J. D. McChesney (1965), "Chemical artifacts from the family labiate", J. Org. Chem. 30: 2931–2934). It can be demonstrated that the freshly cut leaves of rosemary do not contain carnosol (Aeschbach, R. and L. Philippossian (1993), "Carnosic acid obtention and uses", U.S. Pat. No. 5,256,700). Carnosic acid is about 10 times more effective as an antioxidant than carnosol (Aruoma et al., 1992), and it, therefore, is important for the high activity of a rosemary extract to minimize the damage to carnosic acid.

Essential oils are volatile oils which are the aroma and flavor components of organic material. They are used in a variety of products such as incense, aromatherapy oils, perfumes, cosmetics, pharmaceuticals, beverages, and foods. The market for these oils demands consistent high quality and reliable supplies at competitive prices. Essential oils are typically commercially extracted from organic material such as rosemary using steam distillation. In this prior art process, the antioxidants are destroyed, and thermal degeneration of the essential oils may occur.

The antioxidant activity of commercially available rosemary products was compared with rosemary extracts prepared in the laboratory using various solvents for extraction. It was found that the antioxidant activity of commercial rosemary products was in the range of 2–5% when compared to mixed tocopherols. A methanol extract had 10% of the activity of mixed tocopherols. Methanol extraction, moreover, results in a dry powder that is difficult to dissolve into preferred carriers, such as edible oils. Accordingly, there were identified goals to increase the specific activity of extracts of species of the family Labiatae, including rosemary, by optimizing the solvent extraction methodology, to test alternate extraction technologies, and to improve the handling characteristics of the extract.

The investigation into alternate extraction technology had two primary objectives. Firstly, to increase the specific activity of the rosemary extracts further for more efficient formulation into soybean oil or other carrier; and, secondly, to identify technology allowing the removal of the essential oil fraction from the extracted material without oxidative destruction of the carnosic acid. One extraction technique investigated is based on tetrafluoroethane (TFE).

A process for the extraction of antioxidants and essential oils from rosemary preferably meets several criteria. It should be economical and also lead to a liquid or oil antioxidant extract that can be formulated into a homogeneous, soybean oil-based final product that is largely free of odor.

For the foregoing reasons, it is desired that a process be found that simultaneously yields antioxidants and essential oils suitable for further commercial use via a single solvent mix. The present invention solves this problem with sufficiently high yields and purities to be a commercially-viable process.

SUMMARY OF THE INVENTION

This invention is directed to a method of simultaneously extracting antioxidants and essential oils from organic materials and the extract products of the method.

A purpose of the invention is to identify a solvent blend and extraction parameters for the extraction of antioxidants of rosemary while attaining a high specific activity and retaining high extraction yields.

Another purpose of the present invention is to provide a method for extracting antioxidants from rosemary that yields a liquid, oily extract that is readily mixed with a liquid product, such as soybean oil, for incorporation into animal feeds and human foods.

A further purpose of the present invention is to provide a method for extracting essential oils from rosemary in high yields and high purity.

The organic material used during testing was dried, finely ground rosemary of the Arp variety. It is anticipated that the organic material can be any plant of the Labiatae family, and more broadly, any plant material which contains antioxidants and essential oils. It is also expected that any parts of the plant which contain the desired components may be extracted, as well as any form of the plant material (e.g., whole, ground, fresh, or dried).

Tetrafluoroethane was used in the solvent blend. Tetrafluoroethane has a boiling point of –27° C. The technology utilizes the vapor pressure of the solvent at room temperature and allows extraction under mild conditions, therefore minimizing the oxidative decomposition of carnosic acid during the extraction process. Tetrafluoroethane is substantially apolar and is preferably blended with acetone in the extractions of rosemary described here. The advantages of TFE show that it is non-flammable, has a low boiling point, is environmentally acceptable (very low toxicity), and is easily handled. It has been found that at ambient or sub-ambient temperatures, TFE leaves behind the majority of the waxes and other non-fragrant materials normally extracted with conventional solvents (Wilde P. F., 1994. Fragrance Extraction. European Patent No. 0616821A1). Another advantage with the use of TFE is that no distillation must be employed due to its low boiling point. It is anticipated that any hydrofluorocarbon (HFC) with a hydrocarbon backbone of three carbons or fewer (C1–C3) may be used, or mixtures thereof. Acetone and methanol were the organic solvents in the solvent blend. Though methanol alone extracts the antioxidants from rosemary very effectively, it leads to a dry powder extract and an inferior liquid final product after formulation into soybean oil. The optimum TFE-based solvent blend for the extraction of antioxidants from rosemary was identified and extraction parameters were defined. Among numerous solvent blends tested, an 80/15/5 weight percent blend of TFE/methanol/acetone, respectively, proved to be the most effective solvent resulting in a liquid extract with up to 35% of the tocopherol efficacy and an antioxidant yield of about 60% of the rosemary antioxidants. Mixtures of TFE and hexane or butane have been tested as well. Though hexane or butane works, they are not as efficient as acetone and methanol. It is anticipated that similar individual organic solvents added to the TFE may be used as well, or mixtures thereof. Examples include, but are not limited to, ethanol, ethylene chloride, isopropanol, methylene chloride, propylene glycol, and other food grade solvents. Yields may differ with different solvent mixtures, but any similar solvent mixture should simultaneously yield essential oils and antioxidants using the present process.

The organic material and solvent blend are added together in a 1:3 (organic material:solvent blend) or higher (i.e., 1:4, 1:5, etc.) weight ratio to perform the extraction step in any vessel which will be compatible with the components. Since the TFE is preferably added in liquid form, the vessel has to be a pressure vessel which will withstand pressures equal to those required to maintain the TFE in liquid form. The extraction has been carried out at ambient temperatures, but the pressure and temperature may be varied, so long as the TFE and organic solvents remain in liquid form. The extraction appears to be almost instantaneous when dried, finely ground rosemary is used, as there was no appreciable difference in efficacy of products and only small differences in yield whether the extraction is done for 5 minutes or 2 hours. The extraction has been carried out at greater than ambient temperature (up to approximately 40° C.) and found to increase yields (e.g., 7–8% crude extract at standard temperature and pressure and 17% crude extract at 40° C.) with a decline in efficacy of the products and a change in the physical characteristics of the final product due to what is believed to be an increased extraction of longer chain hydrocarbons.

The method for removing the organic material from the solution was filtration. Any suitable separation process known to one skilled in the art which does not interfere with the other steps of the method may be used.

The removal of the solvent blend has been accomplished by evaporation. Specifically, the removal has been in steps in order to remove the solvents selectively. The TFE may be removed by any suitable method known to one skilled in the art. A thin film evaporator is anticipated to be suitable for this process. The organic solvent(s) may be removed by any suitable method known to one skilled in the art as well. A wipe film evaporator is anticipated to be suitable for this process.

Once the TFE is removed, it may be cooled or the pressure increased until it reaches its liquid phase and recycled back for reuse. Removal of the organic solvent(s) in the wipe film evaporator yields the oily, liquid antioxidants. The organic solvent(s) may be further treated by any suitable process known to one skilled in the art, specifically column distillation, to separate the organic solvent(s) from the essential oils. The resulting essential oils are of very high purity (pharmaceutical grade) and surprisingly high yields (compared to previous extraction methods for obtaining essential oils).

DETAILED DESCRIPTION OF THE PREFERRED EMBODIMENTS

Figure 1:
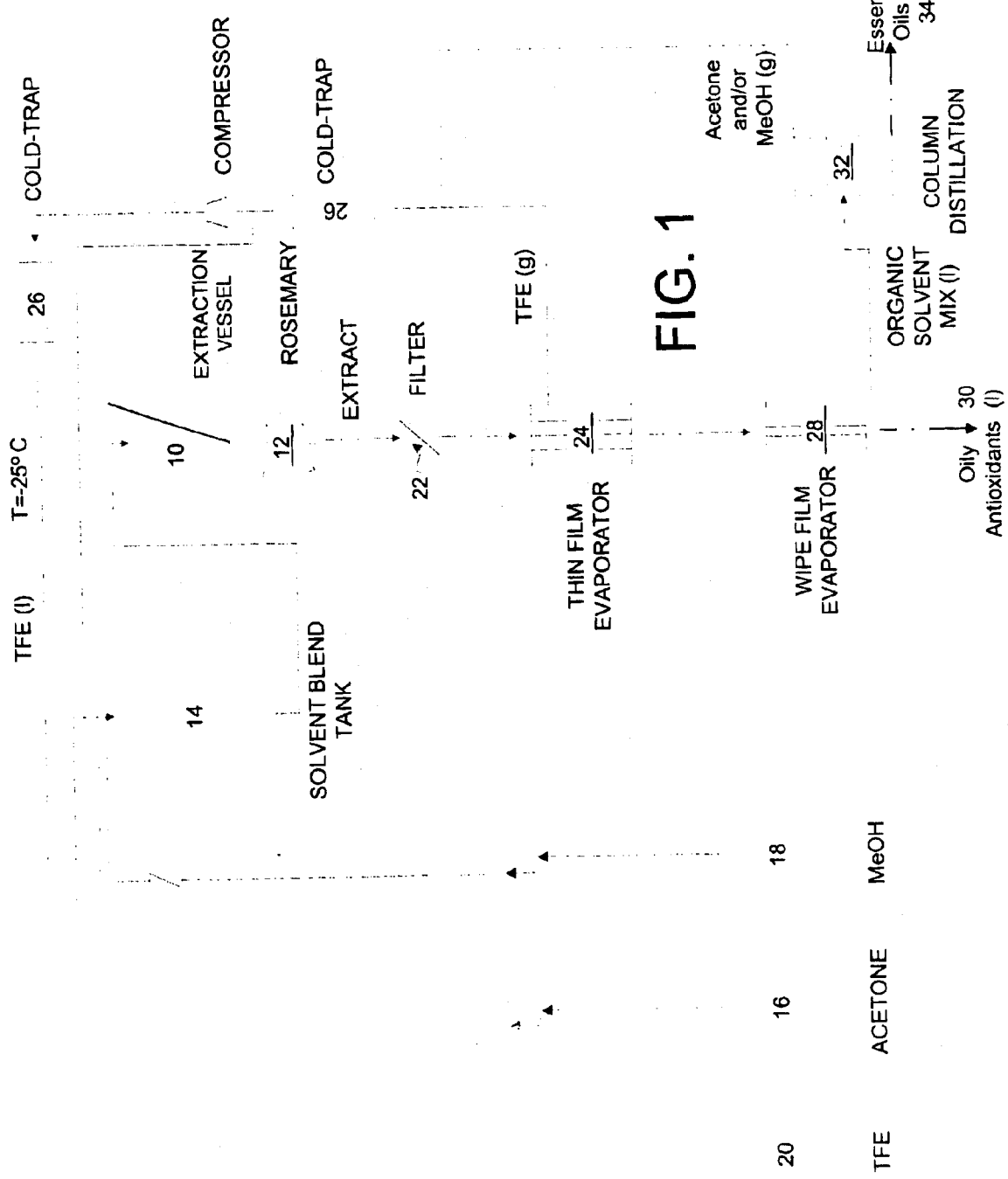
FIG. 1 is a process diagram of the preferred embodiment of the extraction method of the present invention.

The preferred embodiment of the method of the present invention is shown in FIG. 1. The process includes an extraction vessel 10 where the organic material 12 is extracted using the solvent blend at a pressure equal to that necessary to keep the TFE in liquid form and at ambient temperature. The solvent blend is premixed in a solvent blend tank 14 before being added to the extraction vessel 10 where the organic material 12 has been added. The solvents are added to the solvent blend tank 14 from fresh supply tanks, acetone tank 16, methanol tank 18, and TFE tank 20, or alternatively, recycled from the end separation techniques.

After the desired natural organic components are extracted from the organic material 12 after a sufficient residence time, the mixture is passed through a filter 22. The filtered extract then passes through a thin film evaporator 24 where the TFE is removed and the remaining extract passes to the next step. The removed TFE is recycled back through a cold-trap 26 to the TFE tank 20 for reuse.

The TFE-free extract then passes through a wipe film evaporator 28 where the liquid, oily antioxidant portion of the extract 30 is collected and the organic solvent portion of the extract is treated further. The organic solvent portion of the extract passes through column distillation 32 to separate the essential oils 34 from the organic solvents. The organic solvents are condensed in a cold-trap 26 before being recycled back to the solvent blend tank 14.

The methods of this invention are further illustrated by the following experimental examples.

EXAMPLES

Example 1

The invention identifies methods of extracting rosemary with different TFE-based solvents and define preferred extraction conditions. A total of 17 different solvent blends, individually and combined, were used. Data presents the results of the analysis of extracts of rosemary produced from the Arp variety in terms of extraction yield (%) and percent efficacy when compared to 100% mixed tocopherols at equal applications of 500 ppm tested in chicken fat, and rosemary extract/tocopherols equivalency.

All samples were tested in untreated chicken fat at a treatment level of 500 ppm. These samples were then placed into an oxygen bomb pressurized to 50 psi with oxygen, placed in silicon oil at 100° C. and allowed to oxidize. All samples were compared against the induction time of fat treated with 250 ppm 100% mixed tocopherols at a calculated equal concentration level of 500 ppm.

In the data tables, the sample number, the solvent used, percent yield, percent efficacy of tocopherols, and equivalency of rosemary extract to grams of tocopherols are reported. The percent yield was calculated by dividing the yield of rosemary extract by the initial mass of rosemary and multiplication by 100%. The percent efficacy to tocopherols was calculated as follows:

$$\frac{IT_{sample}(500 \text{ ppm}) - IT_{control}}{2(IT_{tocopherols 250 \text{ ppm}} - IT_{control})} \times 100\%$$

where "IT" is the induction time.

Tocopherol equivalent units (g) were calculated using the assumptions that 1.0 kg rosemary was extracted according to the individual methods, and the percent yield and percent efficacy are equivalent from the small scale to the large scale extraction process:

1000 g rosemary×(% yield/100%)×(% efficacy/100%)=tocopherol equivalent (g).

The poultry fat, used as a test matrix, was supplied from Tyson. The various rosemary accessions were obtained from the Chart Co., Papa Geno's Herb Garden, and the North Carolina Botanical Garden. All solvents were purchased from Fisher Scientific Co. The apparatus that the TFE/organic experiments were conducted in was purchased from the Advanced Phytonics facility in Cowfold Grange, Leeming, U.K. All rosemary leaves used in these experiments were from the Arp variety unless otherwise noted.

Method 1

Effect of Solvent Blends on Efficacy

Figure 10:
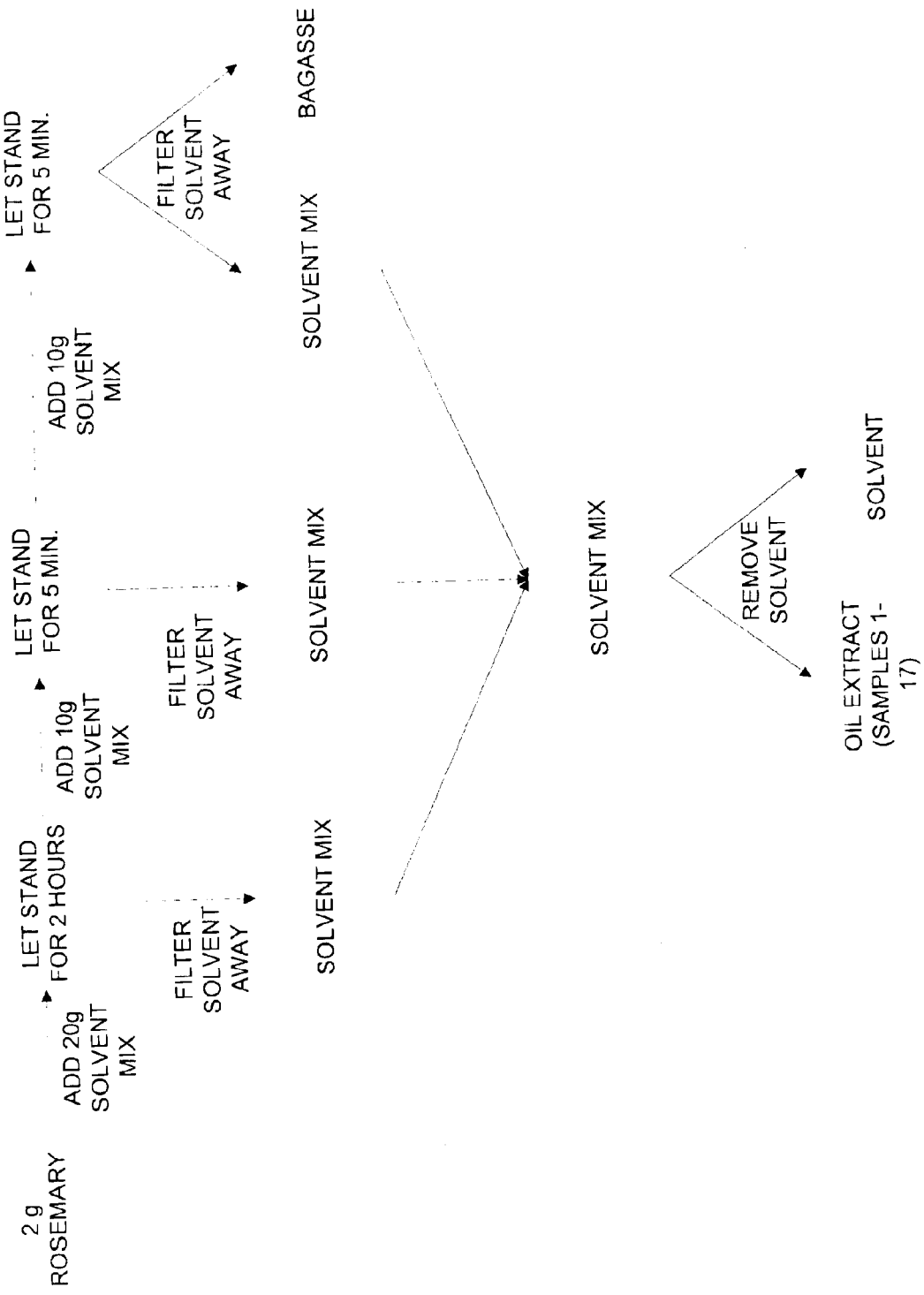
FIG. 10 is a schematic diagram of extraction Method 1 of the present invention.

For samples 1–17, 2.0 g of dried, ground rosemary leaves were introduced into a closed glass vial extractor. The sample was then extracted with 20 g tetrafluoroethane (TFE) or a TFE/solvent mix for two hours. At this time the filtrate was quantitatively transferred into a glass collection vial. The rosemary was then washed with 10.0 g of the extraction solution for five minutes. This liquid portion was added to the first filtrate collected. The rosemary was washed a second time with 10.0 g of the extracting solution and this was also added to the collection vial. After all of the filtrate solutions had been combined, the pressure in the vial was slowly released. After all of the TFE had evaporated, the other organic solution was removed under a stream of nitrogen gas under moderate heating. The extraction process is illustrated diagrammatically in FIG. 10.

Figure 2:
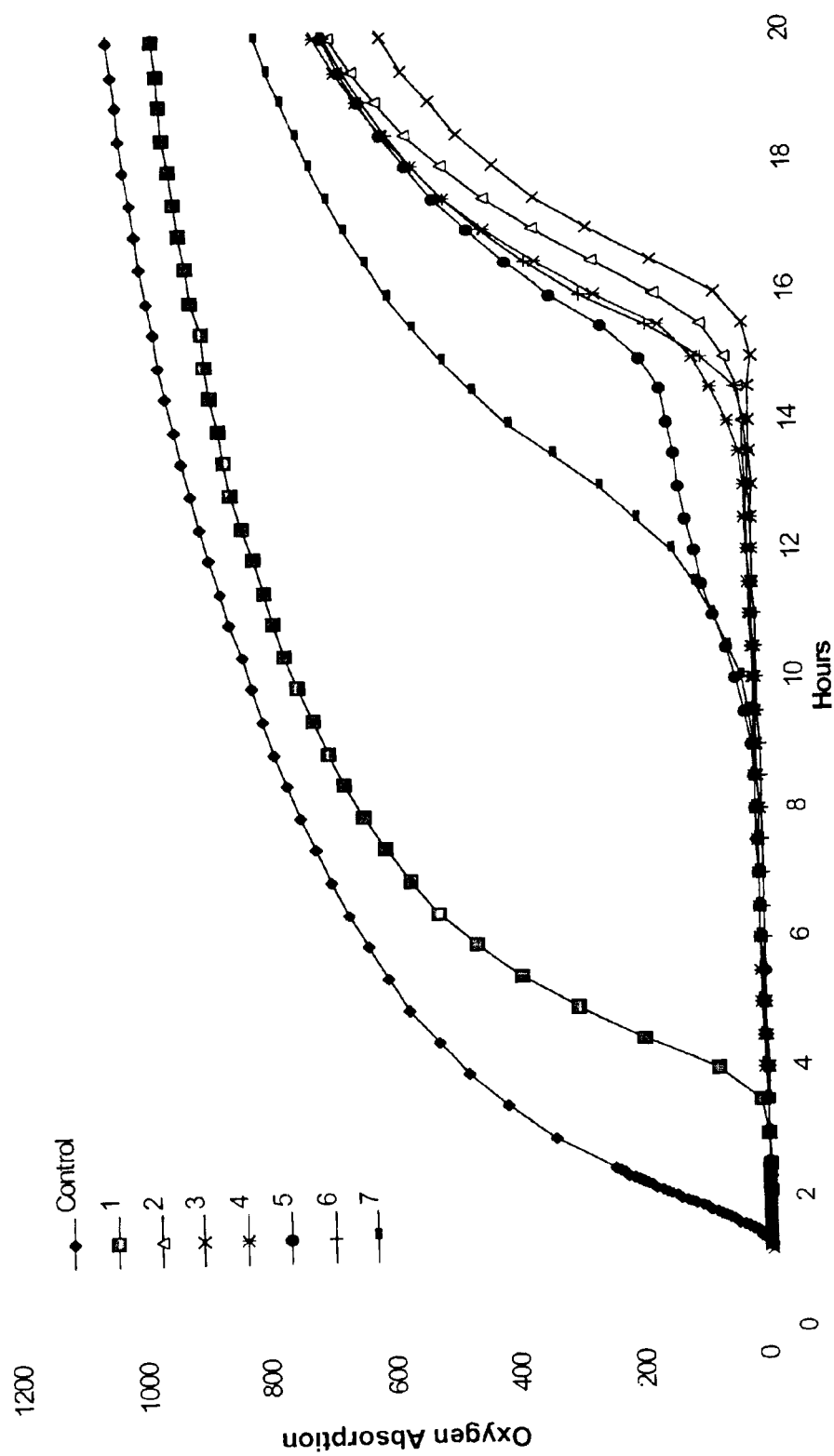
FIG. 2 is a chart of the antioxidant efficacy of a number of samples of rosemary extracted according to described Method 1.

The purpose of this series of experiments (FIG. 2, samples 1–7) was to test the performance of various TFE/acetone blends for the extraction of antioxidants from rosemary. When used alone, TFE results in poor yield with low efficacy. Acetone was added in small amounts to the TFE, initially at a concentration of 5%. The efficacy of the extracts was increased dramatically, up to six-fold, when sample number 2 (95% TFE/5% acetone) was compared to the efficacy of the sample number 1 (100% TFE). As the concentration of the acetone was increased, yields increased steadily while the specific efficacy remained essentially the same after an initial steep increase. It appears that with increasing concentrations of acetone, the blend equally well extracts antioxidant components as well as non-antioxidant components. The yield data are presented in Table 1 and the antioxidant efficacy is illustrated in FIG. 2.

TABLE 1

| No. | Solvent | % Yield | % Efficacy to Tocopherols | Tocopherol Equivalent Units (g) |
|---|---|---|---|---|
| 1 | 100% TFE | 0.95 | 5.84 | 0.555 |
| 2 | 95% TFE/5% acetone | 3.27 | 35.71 | 11.7 |
| 3 | 90% TFE/10% acetone | 5.06 | 37.01 | 18.7 |
| 4 | 85% TFE/15% acetone | 6.50 | 35.71 | 23.21 |
| 5 | 80% TFE/20% acetone | 6.11 | 34.41 | 21.0 |
| 6 | 75% TFE/25% acetone | 6.54 | 34.41 | 22.5 |
| 7 | 70% TFE/30% acetone | 7.49 | 27.92 | 20.9 |

Figure 3:
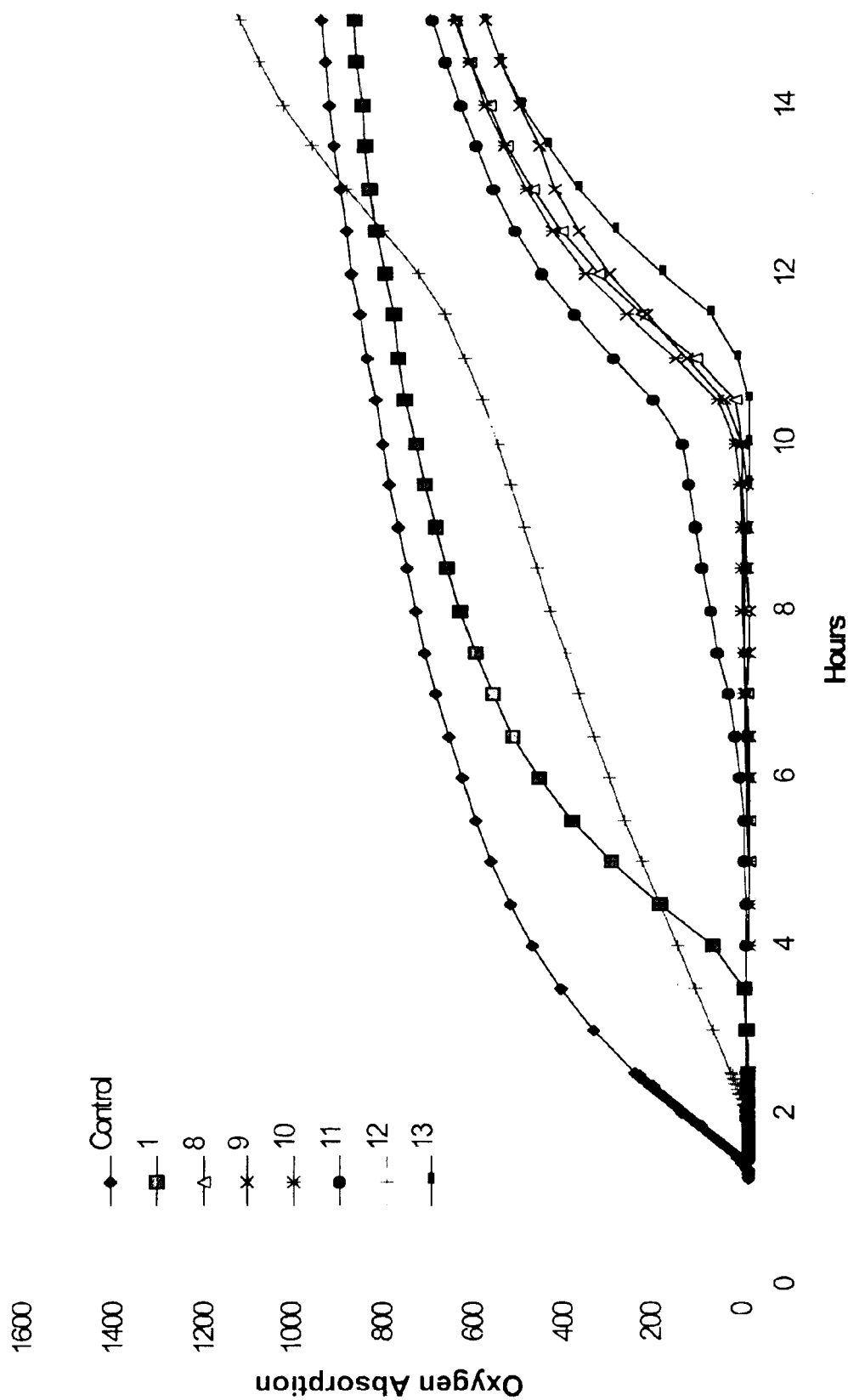
FIG. 3 is a chart of the antioxidant efficacy of a number of samples of rosemary extracted according to described Method 1.

The purpose of the next set of experiments (FIG. 3, samples 1, 8–13) was to test the effect of varying the concentration of hexane when mixed with TFE. Generally, the effect of hexane added to TFE had a less pronounced effect on the performance when compared to the acetone results. However, as was observed with the acetone, hexane was also able to improve the efficacy of the extracts by five-fold when compared to sample number 1 (100% TFE). The yield data are presented in Table 2 and the antioxidant efficacy is illustrated in FIG. 3.

TABLE 2

| No. | Solvent | % Yield | % Efficacy to Tocopherols | Tocopherol Equivalent Units (g) |
|---|---|---|---|---|
| 1 | 100% TFE | 0.95 | 5.84 | 0.555 |
| 8 | 95% TFE/5% hexane | 1.90 | 24.02 | 4.6 |
| 9 | 90% TFE/10% hexane | 2.79 | 24.02 | 6.7 |
| 10 | 85% TFE/15% hexane | 4.85 | 24.02 | 11.6 |
| 11 | 80% TFE/20% hexane | 5.69 | 24.02 | 13.7 |
| 12 | 75% TFE/25% hexane | 5.46 | 26.62 | 14.53 |
| 13 | 70% TFE/30% hexane | 6.40 | 26.62 | 17.0 |

Figure 4:
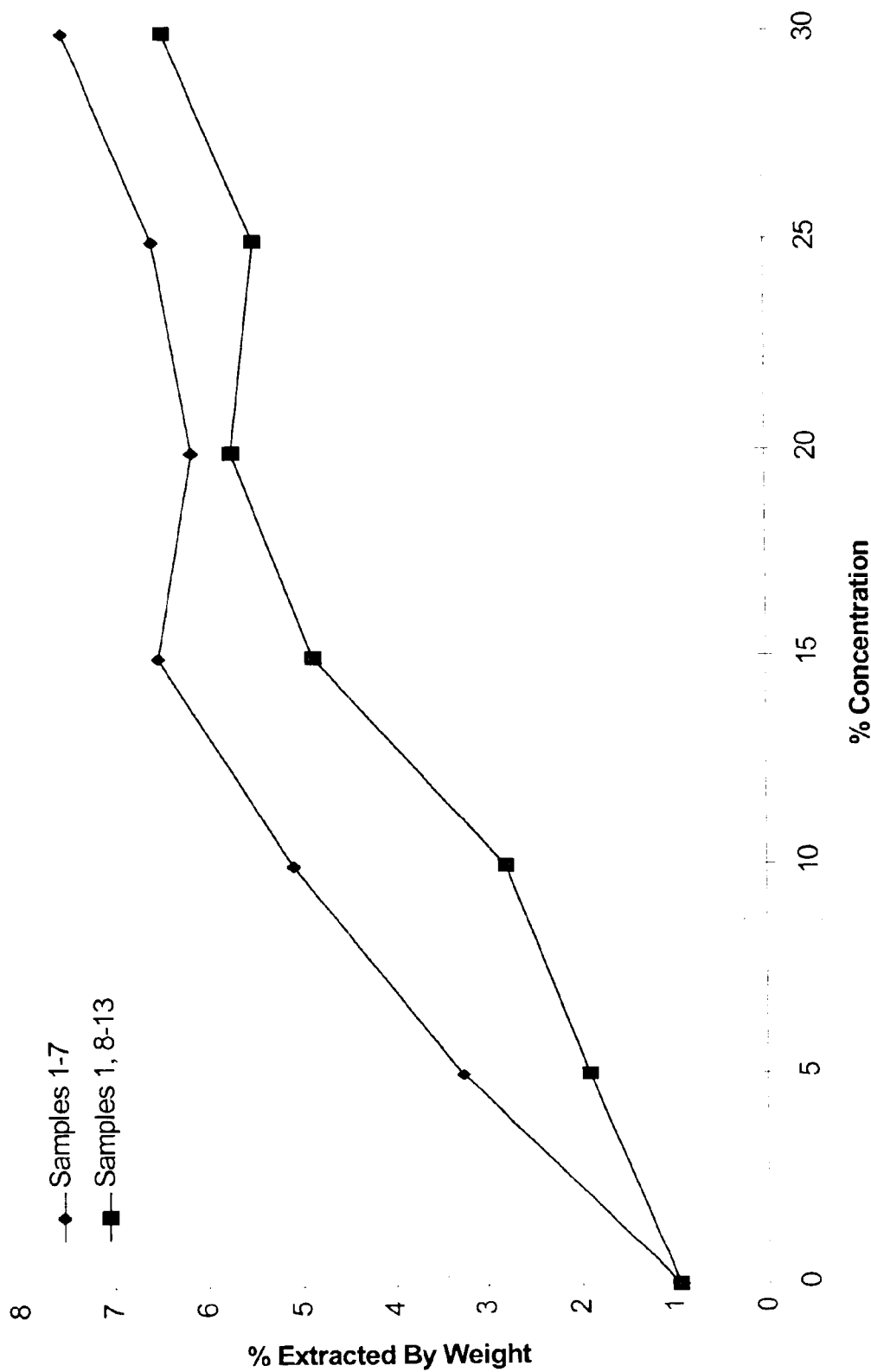
FIG. 4 is a chart of the antioxidant efficacy of a number of samples of rosemary extracted according to described Method 1.
Figure 5:
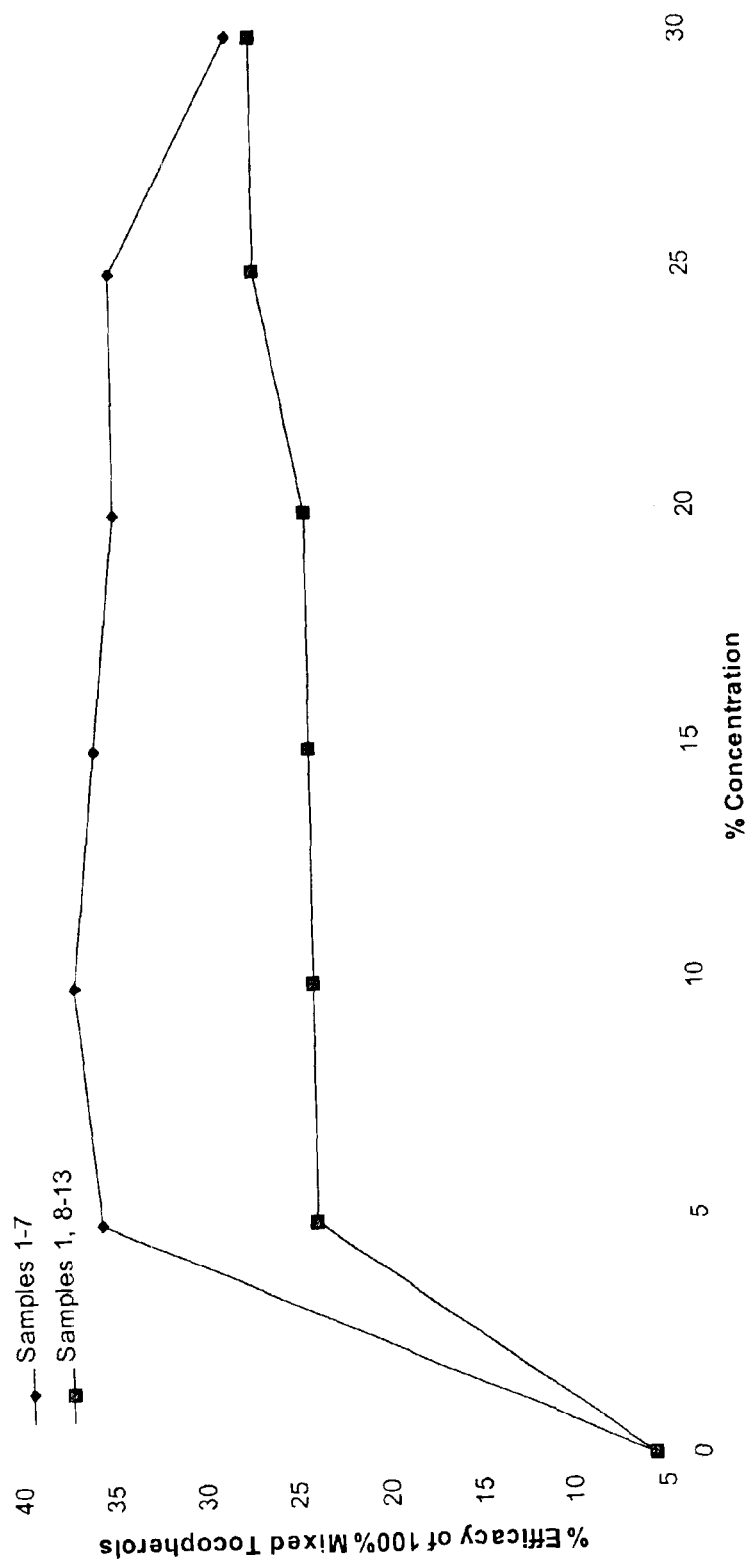
FIG. 5 is a chart of the antioxidant efficacy of a number of samples of rosemary extracted according to described Method 1.

FIGS. 4 and 5 (samples 2–13) compare the two different groups of solvent systems in terms of yields and specific activity. A steady increase in extraction yields can be noted as the TFE is replaced by the two solvents hexane or acetone. As to the specific activity, a rapid increase followed by a long plateau is observed. On average the TFE/acetone extracts outperformed the TFE/hexane extracts by about 10% in terms of specific activity. However, at a concentration of 30% for both solvents, the extracts were approximately equal in efficacy.

Figure 6:
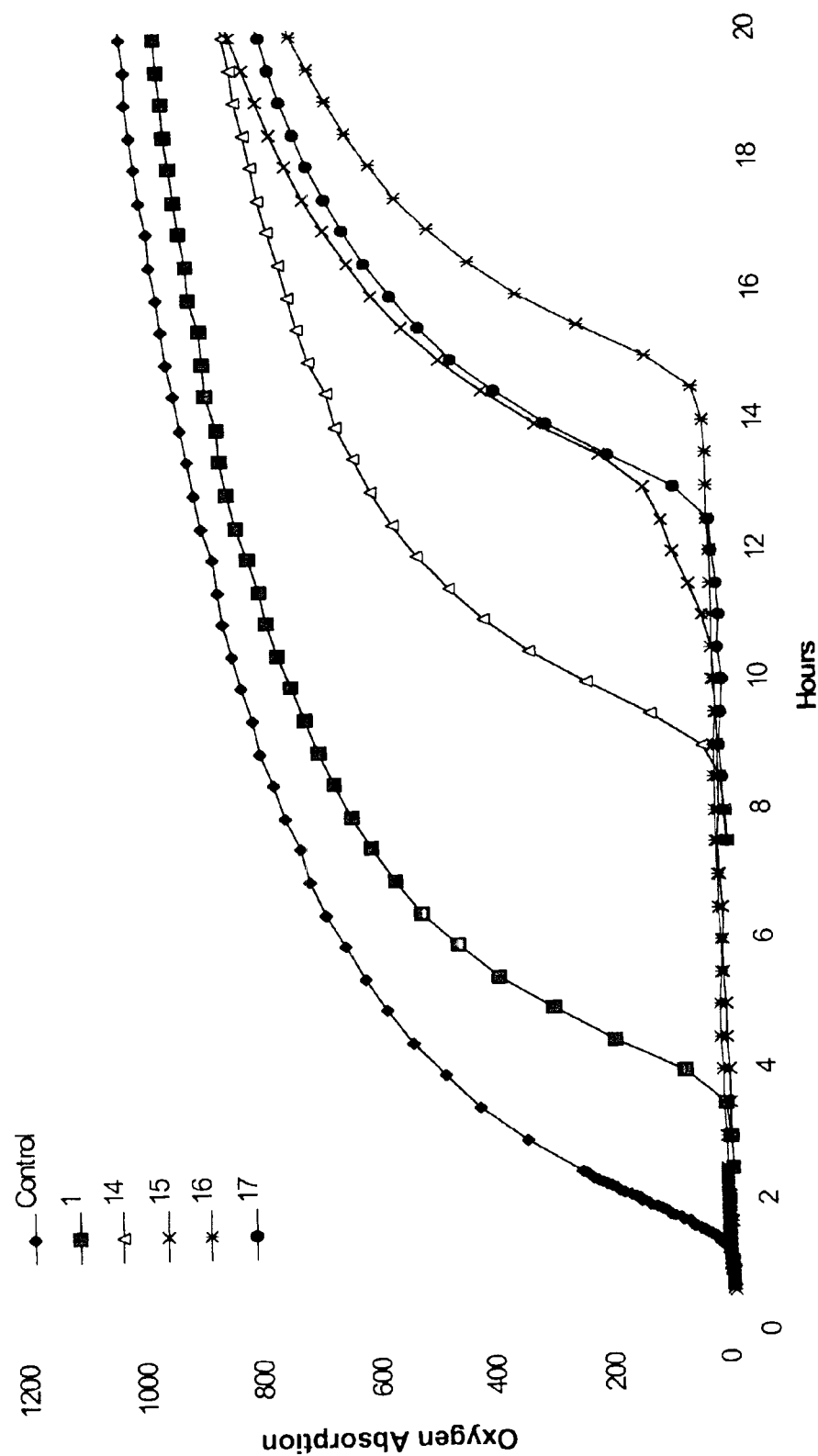
FIG. 6 is a chart of the antioxidant efficacy of a number of samples of rosemary extracted according to described Method 1.

Additional solvents and solvent mixes were tested in an attempt to increase the efficacy and the total antioxidant yield extracted from the rosemary. Table 5 and FIG. 6 (samples 1 and 14–17) display the results of these experiments. When a 90% TFE/10% butane blend was evaluated a three-fold increase in efficacy over sample number 1 (100% TFE) was observed. The TFE/butane extract was equal to a methanol extract. Next, several three-solvent blends were tested. The two solvents mixed with TFE were methanol and acetone, varying in concentration from 5 to 15 percent (see Table 4). Using a solvent mix of 80% TFE/15% MeOH/5% acetone, the extract obtained displayed the highest total yield with a specific efficacy of 29.22% of that of tocopherol and an extraction yield of 10.05%. Methanol in combination with acetone seems to augment extraction yields while maintaining high specific efficacy. The yield data are presented in Table 3 and the antioxidant efficacy is illustrated in FIG. 6.

TABLE 3

| No. | Solvent | % Yield | % Efficacy to Tocopherols | Tocopherol Equivalent Units (g) |
|---|---|---|---|---|
| 1 | 100% TFE | 0.95 | 5.84 | 0.555 |
| 14 | 90% TFE/10% butane | NA | 20.12 | — |
| 15 | 80% TFE/5% MeOH/ 15% acetone | 7.85 | 30.52 | 23.9 |
| 16 | 80% TFE/10% MeOH/ 10% acetone | 6.34 | 34.42 | 21.8 |
| 17 | 80% TFE/15% MeOH/ 5% acetone | 10.05 | 29.22 | 29.4 |

Method 2

Effect of Multiple Extractions on Efficacy and Yield

Figure 11:
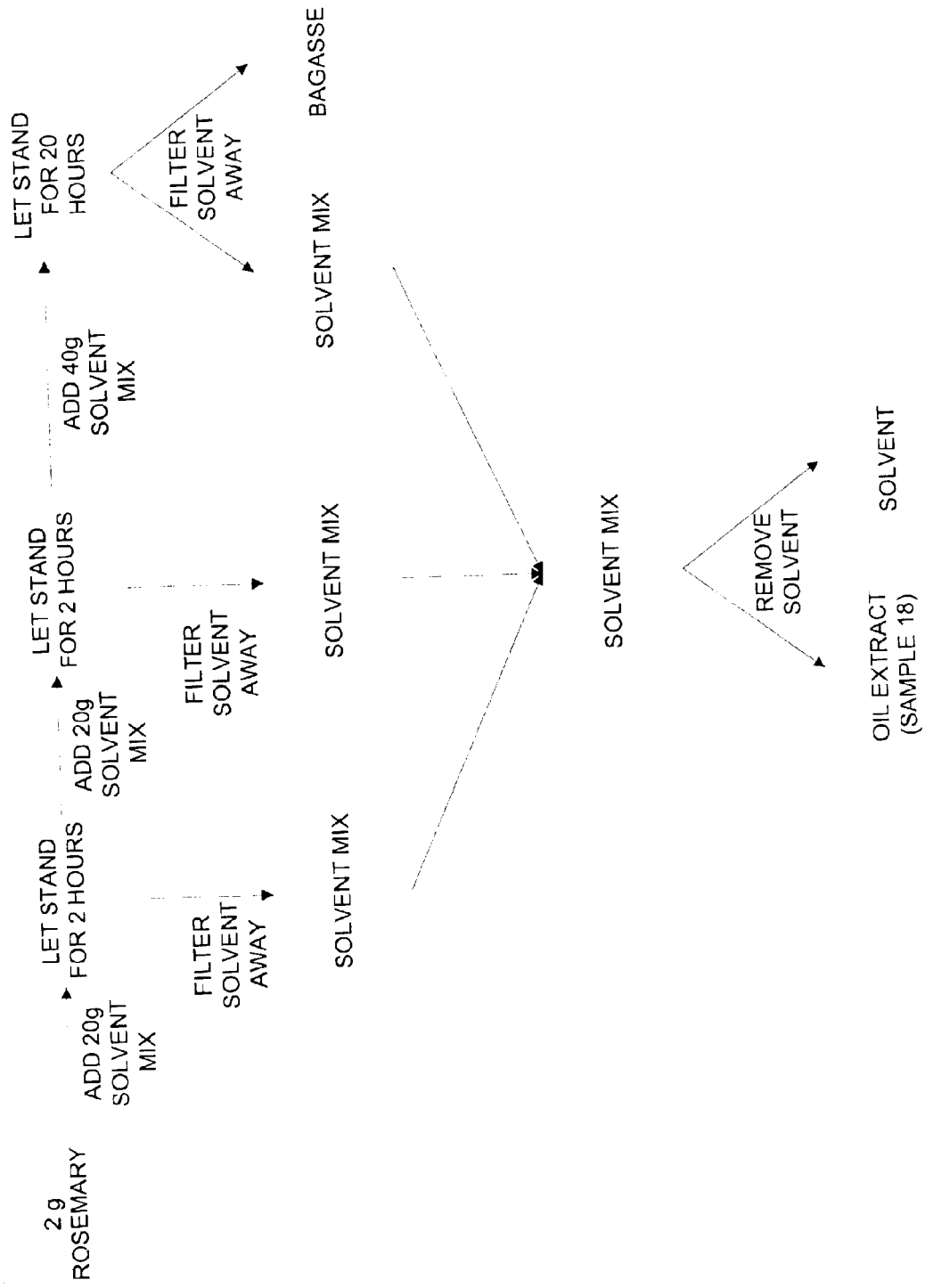
FIG. 11 is a schematic diagram of extraction Method 2 of the present invention.

For sample 18, 2.0 g of dried ground rosemary leaves were introduced into the glass-extracting vial. The sample was then extracted with 20.0 g of 85% TFE/15% acetone for two hours. This was repeated once more. At this time 40.0 g of the solvent mix was added to the extraction vial containing the rosemary. This was allowed to stand for 20 hours. The solvent was then removed and added to the previous two extracts. The TFE was then allowed to evaporate off and the acetone was removed under a stream of nitrogen gas with slight heat. The process is illustrated diagrammatically in FIG. 11.

Figure 7:
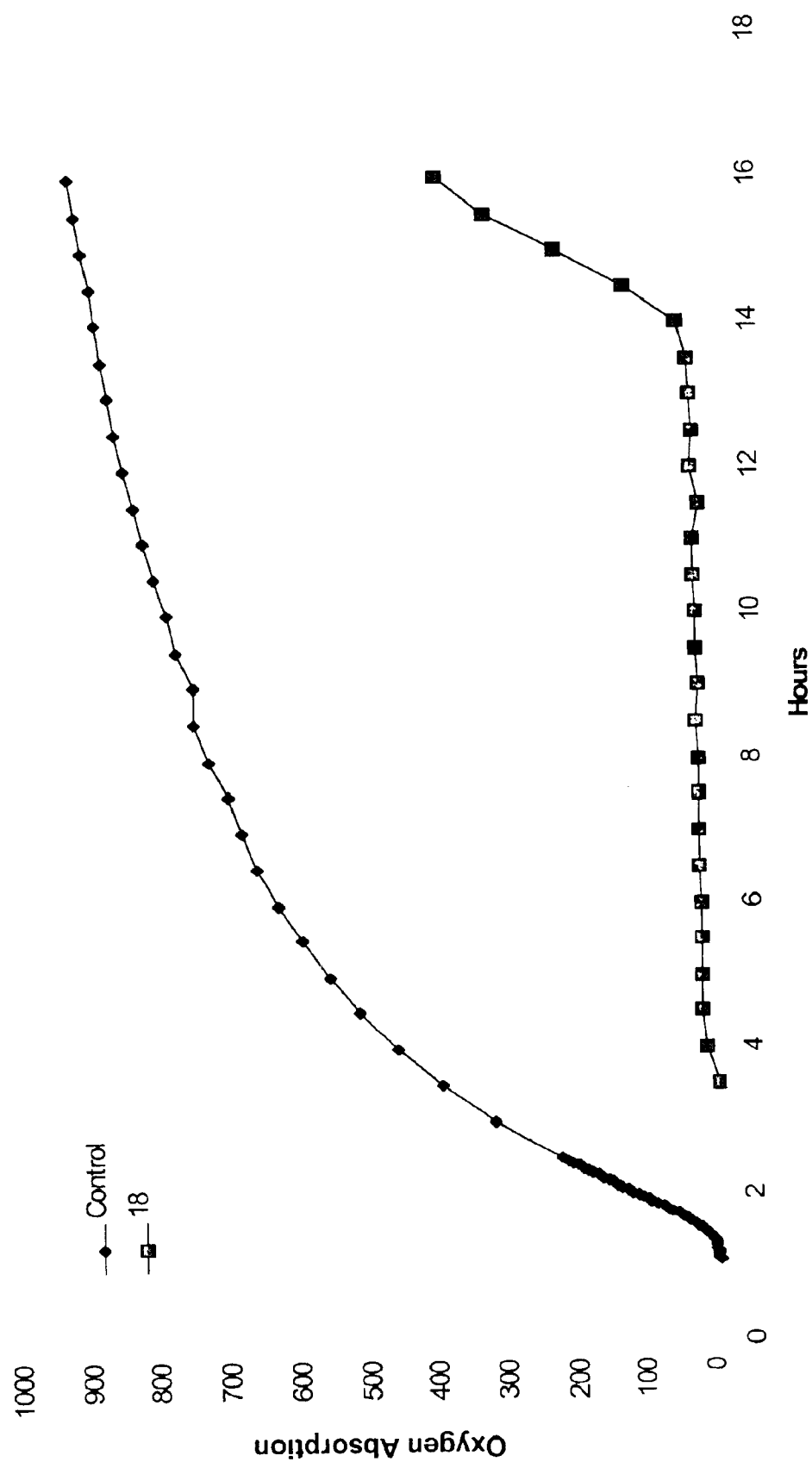
FIG. 7 is a chart of the antioxidant efficacy of a number of samples of rosemary extracted according to described Method 2.

The possibility of attaining higher yields with repeated extractions while retaining the high efficacy of the extracts was explored. FIG. 7 represents the antioxidant activity of sample 18. Sample 18 was produced from the repeated extraction of rosemary over a 24-hour period using 85% TFE/15% acetone. No appreciable increase in the yield or decrease in efficacy was observed when compared to a single extraction. Table 4 presents the yield data.

TABLE 4

| No. | Solvent | % Yield | % Efficacy to Tocopherols | Tocopherol Equivalent Units (g) |
|---|---|---|---|---|
| 18 | 85% TFE/15% acetone | 6.70 | 33.12 | 22.2 |

Method 3

Effect of Extracting a Methanol Extract of Rosemary with a TFE Blend

Sample 19 was prepared by taking 100.0 g of Arp rosemary leaves and extracting it with 600 ml of methanol for 48 hours. This was then filtered and the methanol was evaporated via vacuum rotary evaporator at 40° C. Samples 20 and 22 were prepared by taking 1.0 g of sample 19 and putting it into a glass-extracting vial. For sample 20, 10 g of 85% TFE/15% acetone was added to the 1.0 g of sample 19. This solution was allowed to extract the 1.0 g sample for two hours. This solution was then filtered away from the sample. This was repeated once more. Both solutions were then combined, the TFE was allowed to boil off, and the acetone was removed under a stream of nitrogen gas with slight heat.

Figure 12:
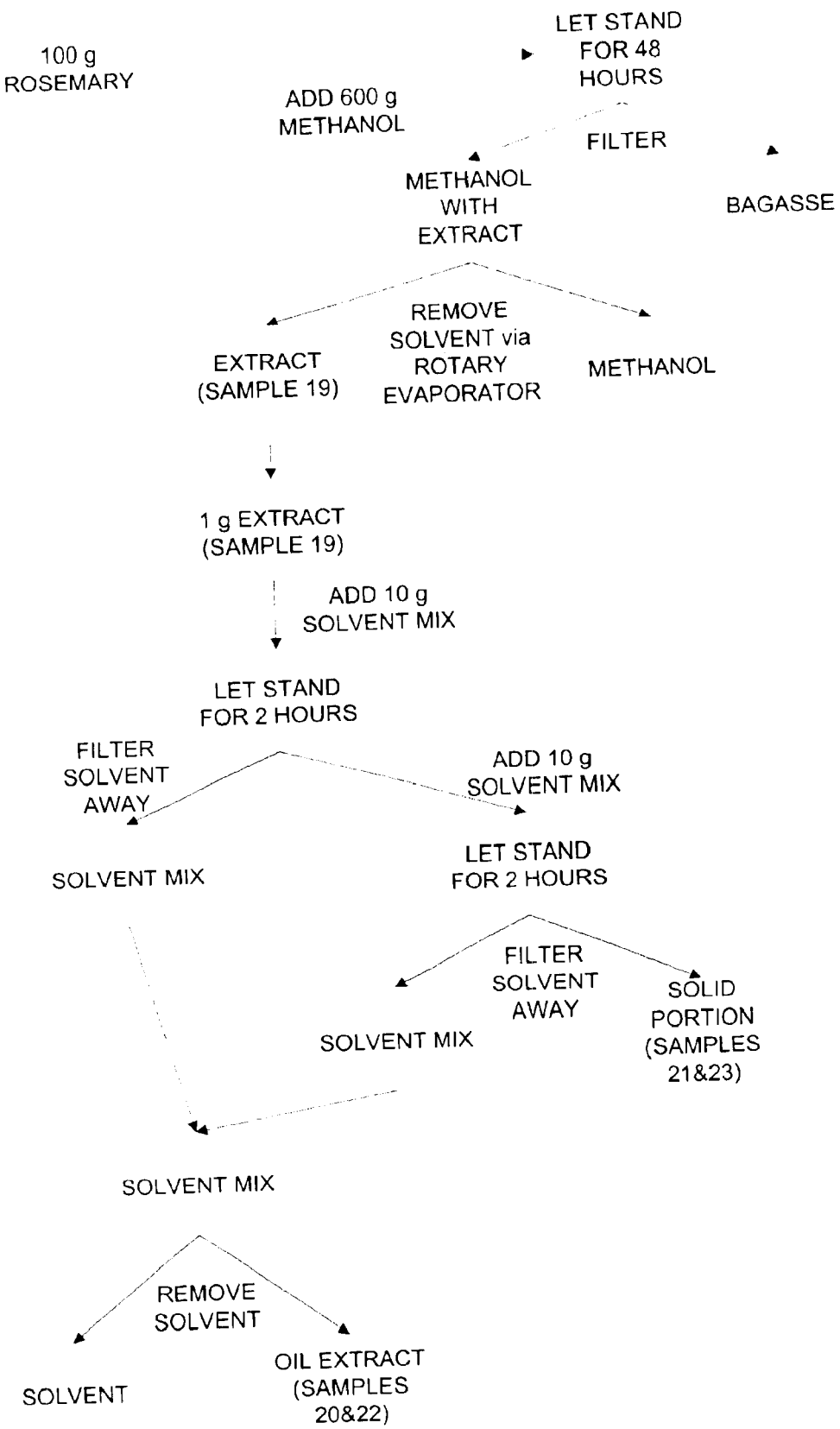
FIG. 12 is a schematic diagram of extraction Method 3 of the present invention.

For sample 22, the same method was followed to prepare sample 20, however, instead of using 85% TFE/15% acetone as the extracting solvent, 70% TFE/30% hexane was used. The material (bagasse) that was left over from the process of preparing samples 20 and 22 was labeled 21 and 23, respectively. This process is illustrated schematically in FIG. 12.

Figure 8:
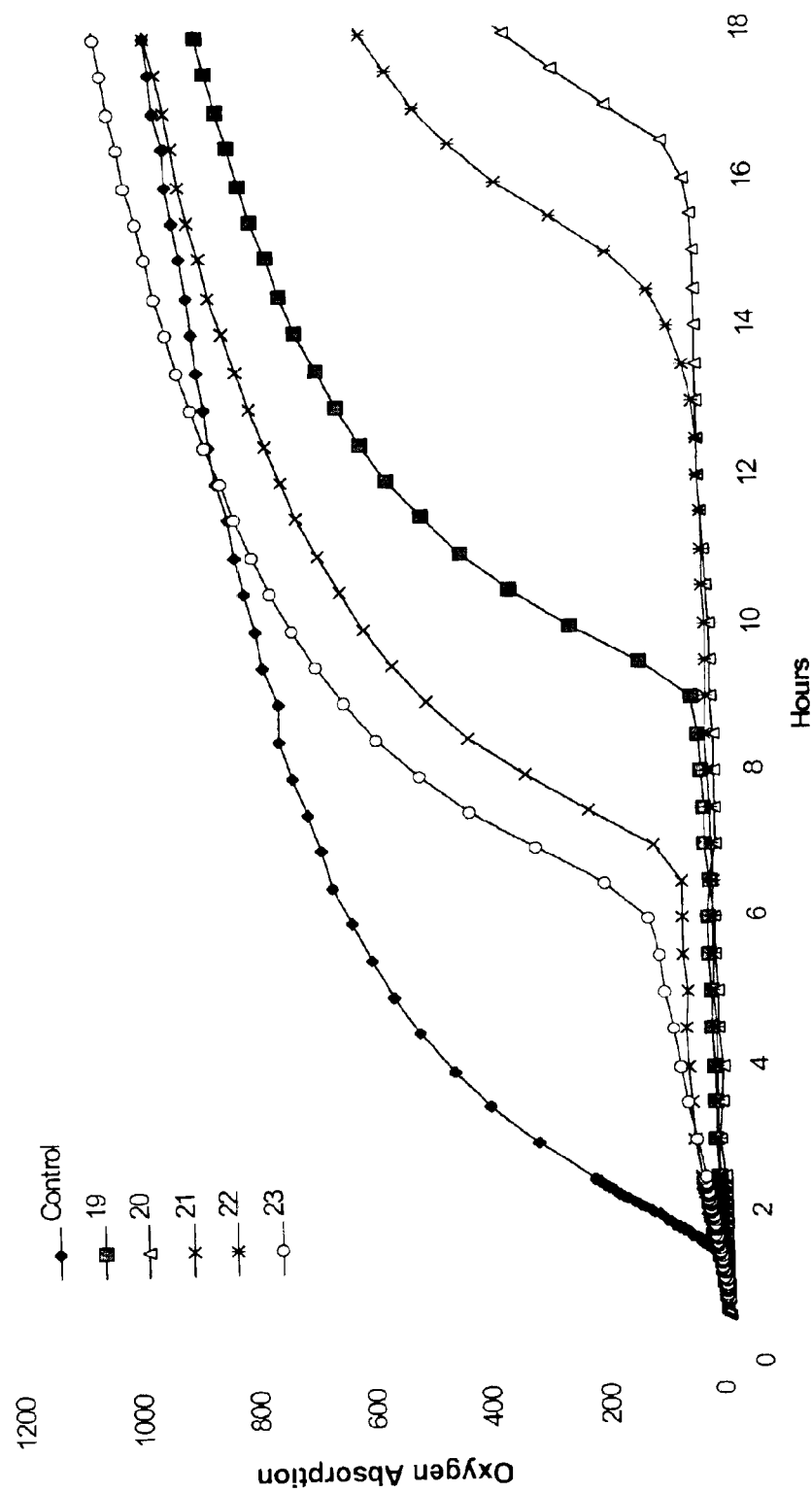
FIG. 8 is a chart of the antioxidant efficacy of a number of samples of rosemary extracted according to described Method 3.

The possibility of utilizing the TFE based extraction process to further deodorize and purify a methanol extract of rosemary was explored (see FIG. 8). Methanol extracts possess close to 100% of the antioxidants from rosemary. With this in mind, TFE mixed with an organic solvent (acetone or hexane) may separate out or extract a larger majority of the antioxidants from a methanol extract over dried, ground rosemary leaves. The test was performed with both, acetone and hexane. Initial tests indicated that the TFE blend solvent extracts were approximately equal to the methanol extracts of dried, ground rosemary. The non-extracted portion, the bagasse, left over from the TFE based extraction (samples 21 and 23), retained a large amount of the antioxidant activity which had 13.64% and 12.34%, respectively, of the tocopherol activity. This residual efficacy indicated the lack of ability of the TFE/organic solvent mix to extract 100% of the antioxidants from a methanol extract of rosemary. Table 5 presents the yield data and FIG. 8 displays the antioxidant efficacy.

TABLE 5

| No. | Solvent | % Yield | % Efficacy to Tocopherols | Tocopherol Equivalent Units (g) |
|---|---|---|---|---|
| 19 | 100% methanol | 27.66 | 20.13 | 36.0 |
| 20 | 85% TFE/15% acetone | 3.91 | 38.31 | 15.0 |
| 21 | Residue | NA | 13.64 | — |
| 22 | 70% TFE/30% hexane | 6.06 | 33.12 | 20.1 |
| 23 | Residue | NA | 12.34 | — |

Method 4

Figure 13:
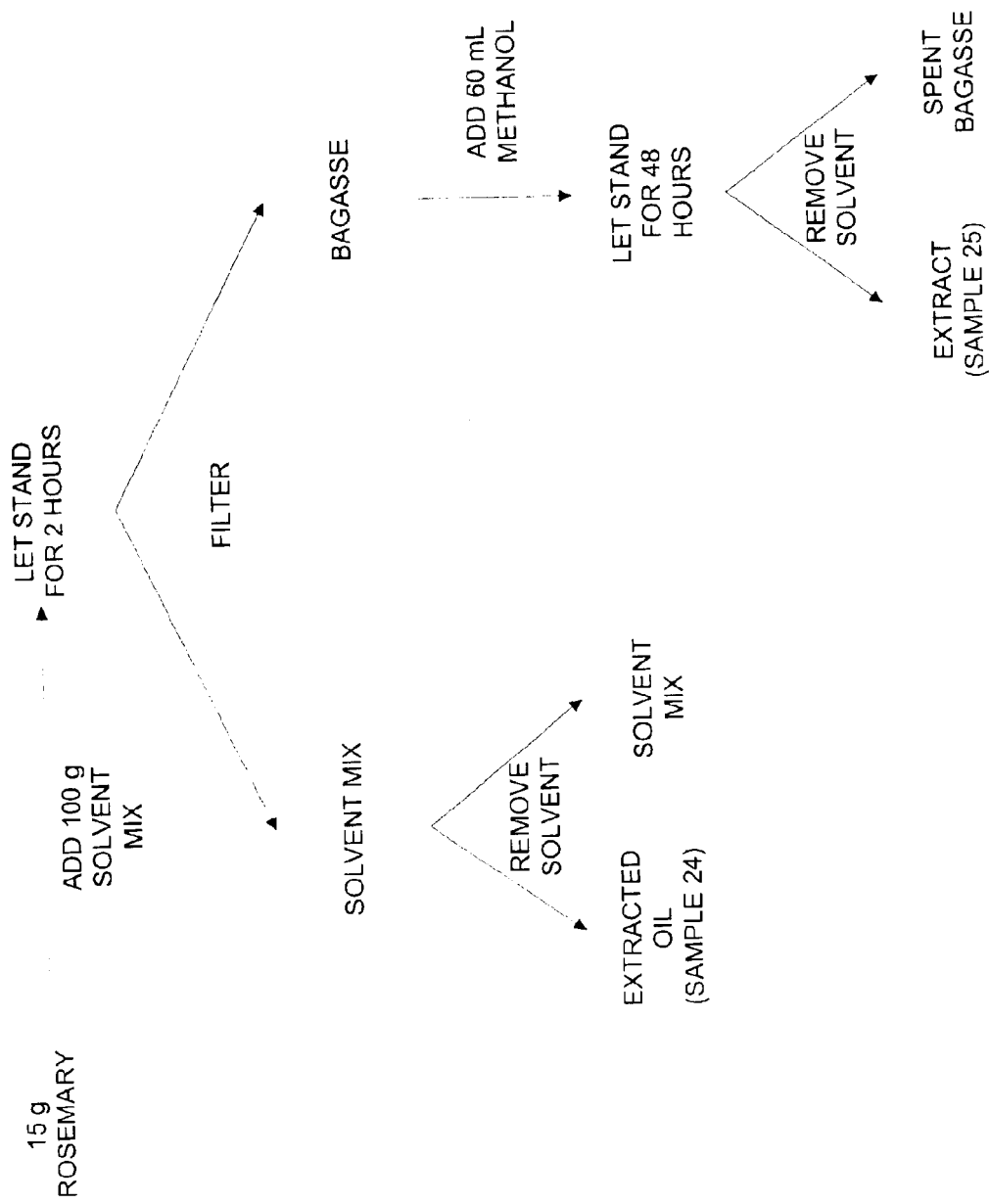
FIG. 13 is a schematic diagram of extraction Method 4 of the present invention.

Extraction of Rosemary with 90% TFE/10% Acetone followed by Extraction of the Bagasse with Methanol Sample 24 was prepared by taking 15.0 g of ground rosemary and placing it into a 250 ml-extracting vial. To this was added 100.0 g of a 90% TFE/10% acetone solvent mixture. This was allowed to stand for two hours and then the solvent was filtered away. The TFE was allowed to boil away and the acetone was removed under a stream of nitrogen gas with slight heat. The remaining bagasse was used to create sample 25. Sample 25 was prepared in the following way. Firstly, the remaining unextracted rosemary left over from the preparation of sample 24 was put into a 250 ml flask and 60 ml of methanol was added. This was allowed to extract for 48 hours. At this point, the solution was filtered and the methanol was removed via vacuum rotary evaporator at 40° C. This process is illustrated diagrammatically in FIG. 13.

Figure 9:
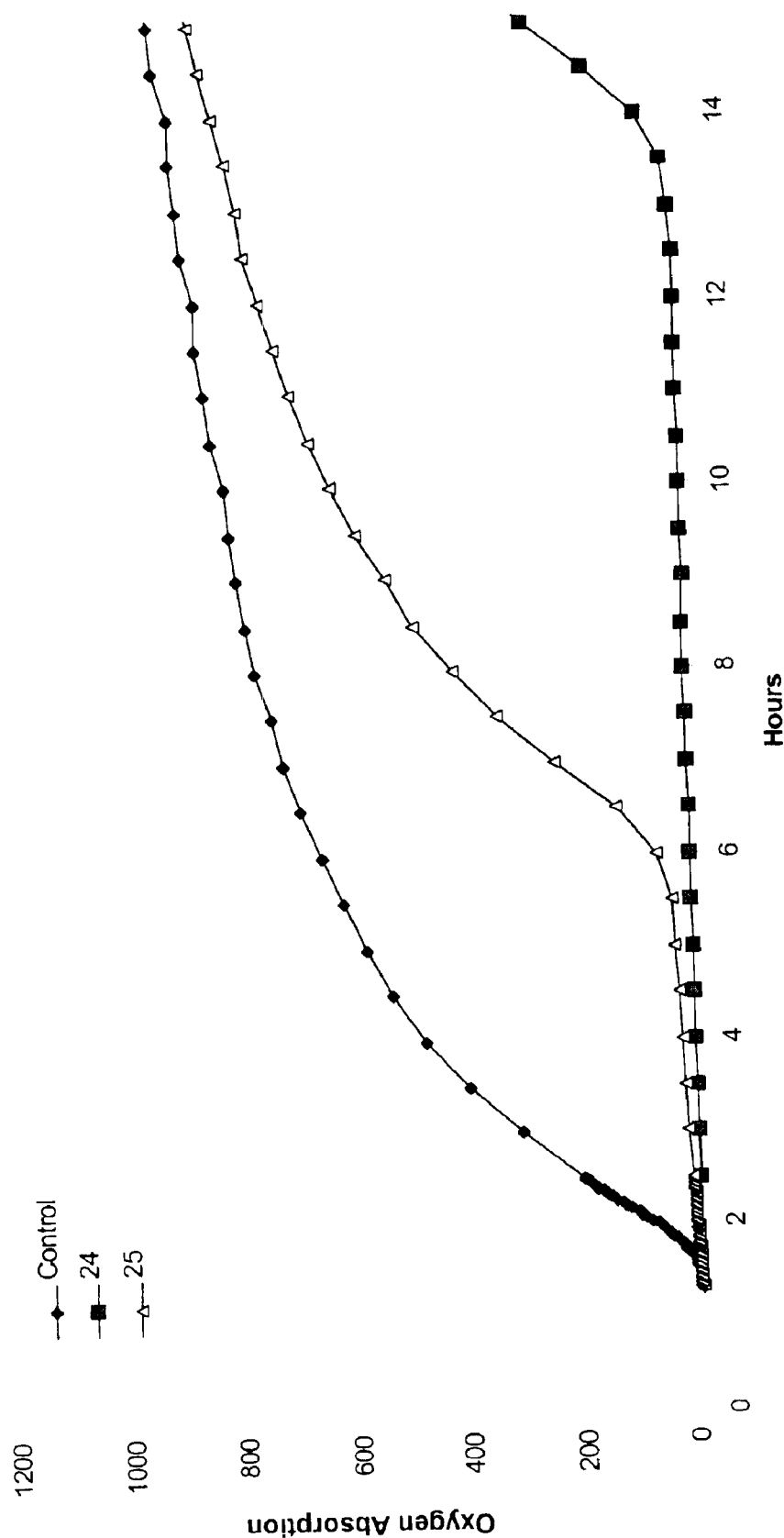
FIG. 9 is a chart of the antioxidant efficacy of a number of samples of rosemary extracted according to described Method 4.

Whether any residual antioxidants are left after an extraction with a TFE blend was investigated (see FIG. 9). A sample of rosemary was extracted with a 90% TFE/10% acetone (sample 24) mix and the residual rosemary material was extracted with methanol (sample 25). The results indicated that a blend of TFE/10% acetone extracted approximately 30% of the antioxidants in rosemary. It appears that the presence of methanol in the solvent blend for the extraction of rosemary is critical for economical yields. The yield data are presented in Table 6 and the antioxidant efficacy displayed in FIG. 9.

TABLE 6

| No. | Solvent | % Yield | % Efficacy to Tocopherols | Tocopherol Equivalent Units (g) |
|---|---|---|---|---|
| 24 | 90% TFE/10% acetone | 4.00 | 31.82 | 12.7 |
| 25 | 100% methanol | 23.7 | 12.34 | 29.24 |

Example 2

Essential Oils Analysis

A sample of 1.8 kg of dried, finely ground rosemary was extracted for 1 hour at a temperature of 25–26° C. at a pressure of 7 bar using 18 kg of a solvent blend of 80% TFE, 12% methanol, and 8% acetone. After removal of the TFE, the extract was subjected to distillation to pull off the acetone and methanol. Analysis of the distillate by gas chromatography followed by mass spectroscopy showed the presence of the essential oils α-pinene, camphene, β-pinene, β-myrcene, eucalyptol, camphor, and caryophyllene.

Although the invention has been described with respect to a preferred embodiment thereof, it is to be also understood that it is not to be so limited since changes and modifications can be made therein which are within the full intended scope of this invention as defined by the appended claims.

What is claimed is:

1. A process for simultaneously extracting at least a first and a second organic component from botanical material, comprising the steps of:
    (a) selecting the botanical material from a plant of the group consisting of rosemary, sage, hyssop, oregano, thyme, basil, marjoram, spearmint, dittany, and lavender;
    (b) contacting the botanical material in a vessel with a solvent blend of tetrafluoroethane and acetone to dissolve the organic components in the solvent blend;
    (c) removing the remaining botanical material from the solution of the organic components and the solvent blend;
    (d) removing the tetrafluoroethane leaving at least the first organic component in the acetone phase; and
    (e) removing the solvent blend to isolate a liquid, oily product containing the first organic component having antioxidant properties from the second organic component.

2. The process of claim 1, further comprising at least one co-solvent selected from the group consisting of ethanol, ethylene chloride, isopropanol, methanol, methylene chloride, and propylene glycol.

3. The process of claim 1, wherein the solvent blend comprises from between about 60% to about 95% tetrafluoroethane.

4. A process for simultaneously extracting at least a first and a second organic component from botanical material, comprising the steps of:
    (a) selecting the botanical material from a plant of the group consisting of rosemary, sage, hyssop, oregano, thyme, basil, marjoram, spearmint, dittany, and lavender;
    (b) contacting the botanical material in a vessel with a solvent blend of tetrafluoroethane and ethanol to dissolve the organic components in the solvent blend;

(c) removing the remaining botanical material from the solution of the organic components and the solvent blend;

(d) removing the tetrafluoroethane leaving at least the first organic component in the ethanol phase; and (e) removing the solvent blend to isolate a liquid, oily product containing the first organic component having antioxidant properties from the second organic component.

5. The process of claim 4, further comprising at least one co-solvent selected from the group consisting of acetone, ethylene chloride, isopropanol, methanol, methylene chloride, and propylene glycol.

6. The process of claim 4, wherein the solvent blend comprises from between about 60% to about 95% tetrafluoroethane.

7. A process for simultaneously extracting at least a first and a second organic component from botanical material, comprising the steps of:

(a) selecting the botanical material from a plant of the group consisting of rosemary, sage, hyssop, oregano, thyme, basil, marjoram, spearmint, dittany, and lavender;

(b) contacting the botanical material in a vessel with a solvent blend of tetrafluoroethane and methanol to dissolve the organic components in the solvent blend;

(c) removing the remaining botanical material from the solution of the organic components and the solvent blend;

(d) removing the tetrafluoroethane leaving at least the first organic component in the methanol phase; and (e) removing the solvent blend to isolate a liquid, oily product containing the first organic component having antioxidant properties from the second organic component.

8. The process of claim 7, further comprising at least one co-solvent selected from the group consisting of acetone, ethanol, ethylene chloride, isopropanol, methylene chloride, and propylene glycol.

9. The process of claim 7, wherein the solvent blend comprises from between about 60% to about 95% tetrafluoroethane.

* * * * *